United States Patent [19]

Hidaka et al.

[11] Patent Number: 5,015,660

[45] Date of Patent: May 14, 1991

[54] MICROBICIDAL/MICROBISTATIC COMPOSITION FOR INDUSTRIAL USE AND METHOD OF USING SAME

[75] Inventors: Yasuhiro Hidaka, Osaka; Toshio Sato, Oita; Masanobu Takahashi, Osaka, all of Japan

[73] Assignee: Yoshitami Pharmaceutical Industries, Ltd., Osaka, Japan

[21] Appl. No.: 438,381

[22] Filed: Nov. 20, 1989

[30] Foreign Application Priority Data

Nov. 21, 1988 [JP] Japan .................. 63-294378

[51] Int. Cl.$^5$ ...................... A01N 33/18; A01N 43/26
[52] U.S. Cl. .................... 514/441; 162/161; 210/764; 514/741
[58] Field of Search ............... 514/441, 741; 162/161; 210/764

[56] References Cited

U.S. PATENT DOCUMENTS

| | | | |
|---|---|---|---|
| 3,871,860 | 3/1975 | Manowitz et al. | 71/67 |
| 3,879,513 | 4/1975 | Shema et al. | 514/441 |
| 4,647,577 | 3/1987 | Umekawa et al. | 514/441 |

FOREIGN PATENT DOCUMENTS

| | | |
|---|---|---|
| 14294 | 1/1977 | Japan . |
| 42603 | 4/1982 | Japan . |
| 2165229 | 4/1986 | United Kingdom . |

*Primary Examiner*—Allen J. Robinson
*Attorney, Agent, or Firm*—Sughrue, Mion, Zinn, Macpeak & Seas

[57] ABSTRACT

A microbicidal/microbistatic composition for industrial use which contains 4,5-dichloro-1,2-dithiol-3-one and bromonitrostyrene and a method of killing or inhibiting the growth of microorganisms or controlling slime formation using the composition.

7 Claims, 1 Drawing Sheet

MICROBICIDAL/MICROBISTATIC COMPOSITION FOR INDUSTRIAL USE AND METHOD OF USING SAME

FIELD OF THE INVENTION

This invention relates to a microbicidal/microbistatic composition for industrial use which contains 4,5-dichloro-1,2-dithiol-3-one and bromonitrostyrene and to a method of using the same.

BACKGROUND OF THE INVENTION 4,5-Dichloro-1,2-dithiol-3-one and $\beta$-bromo-$\beta$-nitrostyrene (hereinafter abbreviated as bromonitrostyrene) to be used in accordance with the invention are known to be biocides for industrial use. Japanese Patent Publication No. 14294/1977 discloses that 4,5-dichloro-1,2-dithiol-3-one is a compound effective in preventing microorganism-caused slime formation in industrial water systems, in particular in white water in paper mills and in cooling water. Japanese Laid-open Patent Application KOKAI No. 7701/1981, Japanese Patent Publication No. 42603/1982 and Japanese Laid-open Patent Application KOKAI No. 91108/1986 mention that the combined use of 4,5-dichloro-1,2-dithiol-3-one and a bromine-containing microbicidal/microbistatic agent can produce a synergistic antimicrobial effect. Thus, it is known that the combined use of 4,5-dichloro-1,2-dithiol-3-one on one hand and a bromoacetate ester (Japanese Laid-open Patent Application KOKAI No. 7701-1971), 2,2-bromonitro-1,3-propanediol (Japanese Patent Publication No. 42603/1982) or dibromonitrilopropionamide (Japanese Laid-open Patent Application KOKAI No. 91108/1986) on the other can exhibit a several times enhanced antimicrobial activity, namely a marked synergism.

4,5-Dichloro-1,2-dithiol-3-one is in practical use as a slimicide in papermaking white water systems and industrial cooling water systems, either alone or in combination with a bromine-containing slimicide.

It is characteristic of 4,5-dichloro-1,2-dithiol-3-one that it produces a rapid and potent microbicidal effect. While that is one of the most desirable characteristics of slimicies, 4,5-dichloro-1,2-dithiol-3-one itself is a relatively expensive compound and cost reduction has been demanded for its economical use. U.S. Pat. No. 3,871,860 discloses that bromonitrostyrene are useful for controlling slime-forming organisms in waters.

SUMMARY OF THE INVENTION

In view of the fact that synergism can be attained by the combined use of 4,5-dichloro-1,2-dithiol-3-one with bromine-containing slimicides or microbicides, the present inventors searched for a bromin-containing compound that can enhance the potent microbicidal activity of 4,5-dichloro-1,2-dithiol-3-one to a further extent and, as a result, found that bromonitrostyrene, more specifically $\beta$-bromo-$\beta$-nitrostyrene, is a compound very suited for that purpose.

It is an object of the invention to provide a microbicidal/microbistatic composition for industrial use which contains 4,5-dichloro-1,2-dithiol-3-one and bromonitrostyrene.

Another object of the invention is to provide a method of killing or inhibiting the growth of microorganisms and thereby controlling slime formation, among others, which comprises using said composition.

DETAILED DESCRIPTION

The invention thus provides:

(1) A microbicidal/microbistatic composition for industrial use which contains 4,5-dichloro-1,2-dithiol-3-one and bromonitrostyrene;

(2) A method of killing or inhibiting the growth of microorganisms in industrial materials and in water systems which comprises using the composition of the invention; and (3) A method of killing or inhibiting the growth of microorganisms and thereby controlling slime formation in paper mill white water systems or in cooling tower water systems which comprises using the composition of the invention.

Bromonitrostyrene, which is to be used in accordance with the invention, can be prepared, for example by subjecting benzaldehyde and nitromethane to dehydration condensation, brominating the resulting $\beta$-nitrostyrene and subjecting the resulting $\alpha,\beta$-dibromo-$\beta$-nitroethylbenzene to dehydrobromination. The product occurs as yellow crystals. This compound is known as a microbicide, in particular a slimicide for papermaking white water systems.

4,5-Dichloro-1,2-dithiol-3-one and bromonitrostyrene are used generally in a mixing ratio of 9:1 to 1:19 by weight, preferably 4:1 to 1:9 by weight. The composition is preferably added as such, namely in the form of a mixture, to targets to be treated. It is also possible, however, to add the respective ingredients separately to such targets to provide the composition according to the invention in situ. For practical use, the composition generally takes the form of a solution of both ingredients in a solvent selected from among, for example N-methyl-2-pyrrolidone, dimethylformamide, mono- and polyalkylene glycols, mono- and polyalkylene glycol monomethyl ethers, and mixtures of these. N-Methyl-2-pyrrolidone is one of preferred solvents from the viewpoints of the solubility of bromonitrostyrene therein and the physical properties thereof. Such solvents can contain a stabilizer or can be used as a mixture. It is recommendable to further add a surfactant to a composition composed of 4,5-dichloro-1,2-dithiol-3-one, bromonitrostyrene and an organic solvent or organic solvent mixture. Said surfactant may be an ordinary dispersing agent and preferably is a nonionic or anionic surfactant selected from among higher alcohol-ethylene oxide adducts, alkylphenolethylene oxide or propylene oxide adducts, alkylphenol-ethylene oxide-propylene oxide adducts, coco fatty acid diethanolamides, ethylenediamine-ethylene oxide-propylene oxide block copolymers, aromatic sulfonic acid salts, aliphatic sulfonic acid salts, and the like.

The composition of the invention preferably contains 4,5-dichloro-1,2-dithiol-3-one and bromonitrostyrene in a total amount of 1 to 50 parts by weight, together with at least 0.01 part by weight of a surfactant, per 100 parts by weight of said compositions, the balance being an organic solvent.

The composition provided by the present invention is used for killing or inhibiting the growth of microorganisms in industrial materials or water systems or for killing or inhibiting the growth of microorganisms in paper mill white water systems or cooling tower water systems to thereby control slime formation therein. More particularly, said composition can be used as a microbicidal/microbistatic composition for papermaking process water in paper and pulp industry, various kinds of cooling water or washing water for industrial use, heavy oil sludge, metal processing oils, textile oils, paints, antifouling paints, paper coating compositions, lattices, pastes, adhesives, etc. In this case, another or other microbicidal agents can be used in combination.

When combined with 4,5-dichloro-1,2-dithiol-3-one, bromonitrostyrene exhibits an excellent synergism in microbicidal activity and surpasses, in synergistic effect, 1,4-bis(bromoacetoxy)butene-2, 2,2-bromonitro-1,3-propanediol and dibromonitrilo propionamide, which are microbicides or slimicides most commonly used among commercially available bromine-containing compounds. The following test results evidence such synergistic effect.

Test Example: Determination of Effective Concentrations

Test compound A: 4,5-Dichloro-1,2-dithiol-3-one
Test compound B: Bromonitrostyrene
Test compound C: Dibromonitrilopropionamide
Test compound D: 2,2-Bromonitro-1,3-propanediol
Test compound E: 1,4-Bis(bromoacetoxy)butene
Test organisms:
 (1) *Bacillus subtilis* (gram-positive bacterium)
 (2) *Pseudomonas aeruginosa* (gram-negative bacterium)
 (3) *Rhodotorula rubra* (yeast)

Test conditions: For test organisms (1) and (2), bouillon medium was used (incubation temperature 37° C.) and, for the test organism (3), potato dextrose medium was used (incubation temperature 27° C.).

Criterion: The concentration at which at least 99.9 percent of the initially viable test organism cells ($10^6$ cells/ml) are killed is defined as an effective concentration.

Test Example 1

Microbicidal Effects on *Bacillus subtilis*

(1) Microbicidal effects of the test compounds used singly

TABLE 1

| Test compound | Concentration (ppm) | Viable cell count (cells/ml) |
|---|---|---|
| A | 100 | $<10^2$ |
|  | 50 | $<10^2$ |
|  | 25 | $<10^2$ |
|  | 12.5 | $<10^2$ |
|  | 10.0 | $<10^2$ |
|  | 5.0 | $<10^2$ |
|  | 2.5 | $<10^2$ |
|  | 1.25 | $<10^2$ |
|  | 0.625 | $8.7 \times 10^3$ |
| B | 100 | $<10^2$ |
|  | 50 | $<10^2$ |
|  | 25 | $<10^2$ |
|  | 12.5 | $<10^2$ |
|  | 10.0 | $<10^2$ |
|  | 5.0 | $<10^2$ |
|  | 2.5 | $4.0 \times 10^2$ |
|  | 1.25 | $>10^7$ |
|  | 0.625 | $>10^7$ |
| C | 10.0 | $<10^2$ |
|  | 5.0 | $<10^2$ |
|  | 2.5 | $<10^2$ |
|  | 1.25 | $<10^7$ |
|  | 0.625 | $>10^7$ |
| D | 1000 | $6 \times 10^7$ |
|  | 500 | $4.9 \times 10^4$ |
|  | 250 | $4.2 \times 10^5$ |
|  | 200 | $>10^7$ |
|  | 100 | $>10^7$ |
|  | 50 | $>10^7$ |

TABLE 1-continued

| Test compound | Concentration (ppm) | Viable cell count (cells/ml) |
|---|---|---|
|  | 25 | $>10^7$ |
| E | 200 | $<10^2$ |
|  | 100 | $<10^2$ |
|  | 50 | $<10^2$ |
|  | 25 | $9 \times 10^2$ |
|  | 12.5 | $>10^7$ |

As is evident from the data shown in Table 1, the effective concentrations of the respective test compounds are 1.25 ppm for A, 2.5 ppm for B, 2.5 ppm for C, 1,000 ppm for D and 25 ppm for E.

(2) Synergistic microbial effects resulting from the combined use of 1,4-dichloro-1,2-dithiol-3-one with the respective bromine-containing compounds The test compounds were used in the concentrations (ppm) shown below in Table 2. For each formulation, viable cells were counted (cells/ml). The results obtained are summarized in Table 3.

TABLE 2

| Test compound | Formulation | | | | |
|---|---|---|---|---|---|
|  | I | II | III | IV | V |
| A | 0.313 | 0.469 | 0.625 | 0.938 | 1.25 |
| B | 0.625 | 0.938 | 1.25 | 1.875 | 2.5 |
| C | 0.625 | 0.938 | 1.25 | 1.875 | 2.5 |
| E | 6.25 | 9.375 | 12.5 | 18.75 | 25 |

[The numerical values in the above table indicate the concentrations (in ppm). The combination of the test compounds A and D was omitted because of the weak microbicidal effect of the test compound D used singly.]

TABLE 3

| Test compound | Formulation | | | | |
|---|---|---|---|---|---|
|  | I | II | III | IV | V |
| A + B | $9 \times 10^2$ | $7 \times 10^2$ | $7 \times 10^2$ | $7 \times 10^2$ | $7 \times 10^2$ |
| A + C | $4.1 \times 10^3$ | $3.2 \times 10^3$ | $9 \times 10^2$ | $8 \times 10^2$ | $7 \times 10^2$ |
| A + E | $5.2 \times 10^3$ | $1.2 \times 10^3$ | $1.0 \times 10^3$ | $8 \times 10^2$ | $6 \times 10^2$ |

As is evident from the data shown in Table 3, the effective concentrations of the test compounds are: 0.313 ppm + 0.625 ppm for A + B, 0.625 ppm + 1.25 ppm for A + C, and 0.938 ppm + 18.75 ppm for A + E.

Test Example 2

Microbicidal Effects on *Pseudomonas aeruginosa*

(1) Microbicidal effects of the test compounds used singly

TABLE 4

| Test compound | Concentration (ppm) | Viable cell count (cells/ml) |
|---|---|---|
| A | 50 | $<10^2$ |
|  | 25 | $<10^2$ |
|  | 12.5 | $<10^2$ |
|  | 6.25 | $<10^2$ |
|  | 3.125 | $1.6 \times 10^3$ |
|  | 1.563 | $2.1 \times 10^5$ |
|  | 0.5 | $>10^7$ |
|  | 0.25 | $>10^7$ |
|  | 0.125 | $>10^7$ |
|  | 0.0625 | $>10^7$ |
| B | 100 | $<10^2$ |
|  | 50 | $1.1 \times 10^4$ |
|  | 25 | $1.5 \times 10^4$ |
|  | 12.5 | $1.9 \times 10^4$ |
|  | 6.25 | $8.5 \times 10^4$ |

TABLE 4-continued

| Test compound | Concentration (ppm) | Viable cell count (cells/ml) |
|---|---|---|
| C | 10.0 | $<10^2$ |
|  | 5.0 | $<10^2$ |
|  | 2.5 | $<10^2$ |
|  | 1.25 | $>10^7$ |
|  | 0.625 | $>10^7$ |
| D | 2000 | $8.0 \times 10^3$ |
|  | 1500 | $4.4 \times 10^4$ |
|  | 1000 | $1.4 \times 10^5$ |
|  | 500 | $>10^7$ |
|  | 250 | $>10^7$ |
| E | 200 | $<10^2$ |
|  | 100 | $2.9 \times 10^3$ |
|  | 50 | $8.0 \times 10^5$ |
|  | 25 | $>10^7$ |
|  | 12.5 | $>10^7$ |
|  | 6.25 | $>10^7$ |

As is evident from the data given in Table 4, the effective concentrations of the respective test compounds are: 3.125 ppm for A, 50 ppm for B, 2.5 for C, 2,000 ppm or more for D, and 200 ppm for E.

(2) Synergistic microbicidal effects resulting from the combined use of 4,5-dichloro-1,2-dithiol-3-one with the respective bromine-containing compounds The test compounds were used in the concentrations (ppm) shown below in Table 5. For each formulation, viable cells were counted (cells/ml). The results obtained are summarized in Table 6.

TABLE 5

| Test compound | Formulation | | | | |
|---|---|---|---|---|---|
|  | I | II | III | IV | V |
| A | 1.563 | 2.344 | 3.125 | 4.688 | 6.25 |
| B | 25 | 37.5 | 50 | 75 | 100 |
| C | 0.625 | 0.938 | 1.25 | 1.875 | 2.5 |
| E | 50 | 75 | 100 | 150 | 200 |

[The numerical values shown in the above table indicate the concentration (in ppm). The combination of the test compounds A and D was omitted because of the weak microbicidal effect of the test compound D used singly.]

TABLE 6

| Test compound | Formulation | | | | |
|---|---|---|---|---|---|
|  | I | II | III | IV | V |
| A + B | $<10^2$ | $<10^2$ | $<10^2$ | $<10^2$ | $<10^2$ |
| A + C | $3.9 \times 10^3$ | $1.2 \times 10^3$ | $<10^2$ | $<10^2$ | $<10^2$ |
| A + E | $9 \times 10^2$ | $<10^2$ | $<10^2$ | $<10^2$ | $<10^2$ |

As is evident from the data given in Table 6, the effective concentrations of the respective test compounds are: 1.563 ppm + 25 ppm or less for A + B, 3.125 ppm + 1.25 ppm for A + C, and 2.344 ppm + 75 ppm for A + E.

Test Example 3

Microbicidal Effects on *Rhodotorula rubra*

(1) Microbicidal effects of the compounds used singly

TABLE 7

| Test compound | Concentration (ppm) | Viable cell count (cells/ml) |
|---|---|---|
| A | 200 | $<10^2$ |
|  | 100 | $<10^2$ |
|  | 50 | $<10^2$ |
|  | 12.5 | $<10^2$ |

TABLE 7-continued

| Test compound | Concentration (ppm) | Viable cell count (cells/ml) |
|---|---|---|
|  | 6.25 | $<10^2$ |
|  | 5.0 | $<10^2$ |
|  | 2.5 | $<10^2$ |
|  | 1.25 | $<10^2$ |
|  | 0.625 | $4.9 \times 10^5$ |
| B | 100 | $<10^2$ |
|  | 50 | $<10^2$ |
|  | 25 | $<10^2$ |
|  | 12.5 | $<10^2$ |
|  | 6.25 | $4.1 \times 10^3$ |
|  | 3.125 | $>10^7$ |
|  | 1.563 | $>10^7$ |
| C | 1000 | $<10^2$ |
|  | 500 | $<10^2$ |
|  | 250 | $<10^2$ |
|  | 125 | $<10^2$ |
|  | 100 | $<10^2$ |
|  | 50 | $<10^2$ |
|  | 25 | $<10^2$ |
|  | 12.5 | $>10^7$ |
|  | 6.25 | $>10^7$ |
| D | 1000 | $<10^2$ |
|  | 500 | $<10^2$ |
|  | 250 | $1.3 \times 10^5$ |
|  | 125 | $>10^7$ |
|  | 62.5 | $>10^7$ |
| E | 200 | $<10^2$ |
|  | 100 | $<10^2$ |
|  | 50 | $>10^7$ |
|  | 25 | $>10^7$ |
|  | 12.5 | $>10^7$ |
|  | 6.25 | $>10^7$ |

As is evident form the data shown in Table 7, the effective concentrations of the respective test compounds are 1.25 ppm for A, 12.5 ppm for B, 25 ppm for C, 500 ppm for D and 100 ppm for E.

(2) Synergistic microbicidal effects resulting from the combined use of 4,5-dichloro-1,2-dithiol-3-one with the respective bromine-containing compounds The test compounds were used in the concentration (ppm) shown below in Table 8. For each formulation, viable cells were counted (cells/ml). The results thus obtained are summarized in Table 9.

TABLE 8

| Test compound | Formulation | | | | |
|---|---|---|---|---|---|
|  | I | II | III | IV | V |
| A | 0.313 | 0.469 | 0.625 | 0.938 | 1.25 |
| B | 3.125 | 4.688 | 6.25 | 9.375 | 12.5 |
| C | 6.25 | 9.375 | 12.5 | 18.75 | 25 |
| E | 25 | 37.5 | 50 | 75 | 100 |

[The numerical values shown in the above table indicate the concentrations (in ppm). The combination of the compounds A and D was omitted because of the weak microbicidal effect of the test compound D used singly.]

TABLE 9

| Test compound | Formulation | | | | |
|---|---|---|---|---|---|
|  | I | II | III | IV | V |
| A + B | $6.8 \times 10^5$ | $<10^2$ | $<10^2$ | $<10^2$ | $<10^2$ |
| A + C | $4.4 \times 10^4$ | $<10^2$ | $<10^2$ | $<10^2$ | $<10^2$ |
| A + E | $4.3 \times 10^4$ | $3.1 \times 10^4$ | $<10^2$ | $<10^2$ | $<10^2$ |

As is evident from the data shown above in Table 9, the effective concentrations of the respective test compounds are: 0.469 ppm + 4.668 ppm for A + B, 0.469 ppm+9.375 ppm for A+C, and 0.625 ppm+50 ppm for A+E.

Test Example: Testing by the Two-Dimensional Dilution Method

The minimum inhibitory concentrations of various combinations of 4,5-dichloro-1,2-dithiol-3-one and bromonitrostyrene against *Bacillus subtilis* and *Pseudomonas aeruginosa* were determined by the two-dimensional dilution method (cf. Japanese Patent Publication No. 50642/1984).

It was confirmed that the combined use of both the ingredients produces a synergistic effect. Synergism is significant in the 4,5-dichloro-1,2-dithiol-3-one/bromonitrostyrene weight ratio range of 9:1 to 1:19. It is particularly significant in the weight ratio range of 4:1 to 1:9.

Test compound A: 4,5-dichloro-1,2-dithiol-3-one
Test compound B: Bromonitrostyrene Test conditions and criterion: Bouillon medium is used and, after 24 hours of shake culture at 37° C., whether there is the growth of the test organism observable is judged.

Test Example 4

Minimum inhibitory concentrations (in ppm) attainable by the combined use of compounds A and B as determined against *Bacillus subtilis* by the two-dimensional dilution method (Table 10)

TABLE 10

| Test compound A | Test compound B |
|---|---|
| 6.3 | — |
| 1.6–3.2 | 1.0–2.0 |
| 0.8–1.6 | 2.0–4.0 |
| 0.4–0.8 | 4.0–7.9 |
| 0.2–0.4 | 7.9–10 |
| 0.1–0.2 | 10–13 |
| — | 15.6 |

The above results are graphically shown in FIG. 1. FIG. 1 clearly indicated that the composition of the invention has a remarkably significant synergistic effect on *Bacillus subtilis*.

Test Example 5

Minimum inhibitory concentrations (ppm) attainable by the combined use of test compounds A and B as determined against *Pseudomonas aeruginosa* by the two-dimensional dilution method (Table 11)

TABLE 11

| Test compound A | Test compound B |
|---|---|
| 6.3 | — |
| 1.6–3.2 | 1.0–4.0 |
| 0.8–1.6 | 4.0–7.9 |
| 0.4–0.8 | 7.9–11 |
| 0.2–0.4 | 12–13.5 |
| 0.1–0.2 | 14–15.6 |
| — | 15.6 |

The results shown above are graphically shown in FIG. 2. As is evident from FIG. 2, the composition according to the invention shows a marked synergistic effect on *Pseudomonas aeruginosa*.

Figure 1:
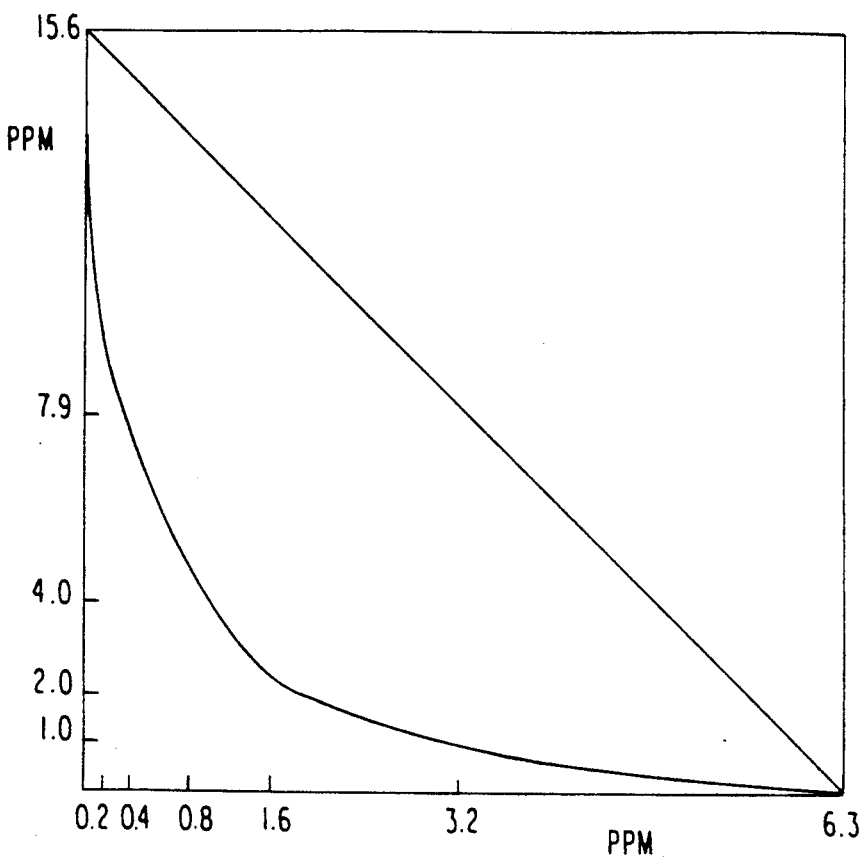
FIG. 1 and FIG. 2 are graphical representations of the minimum inhibitory concentrations of the microbicidal/microbistatic compositions according to the invention as determined against *Bacillus subtilis* and *Pseudomonas aeruginosa*, respectively, by the two-dimensional dilution method. The minimum inhibitory 4,5-dichloro-1,2-dithiol-3-one concentration is on the abscissa and the minimum inhibitory bromonitrostyrene concentration is on the ordinate.
Figure 2:
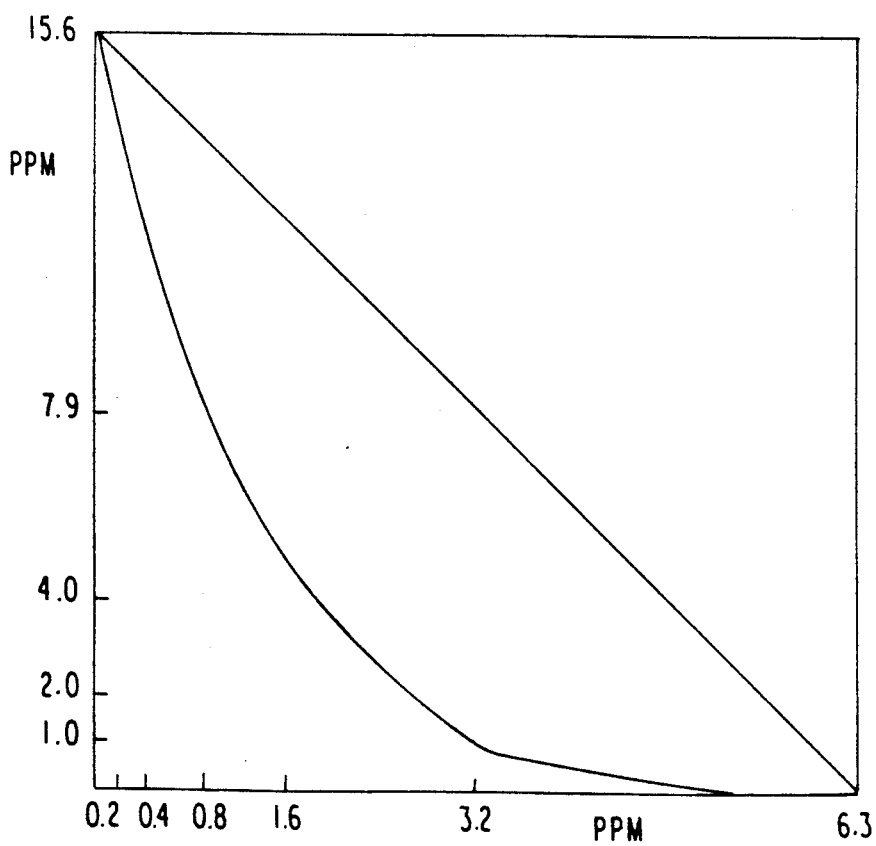

The following formulation examples are further illustrative of the present invention but by no means limitative of the scope thereof.

Formulation Example 1

| | Percent by weight |
|---|---|
| 4,5-Dichloro-1,2-dithiol-3-one | 1.5 |
| Bromonitrostyrene | 1.5 |
| N-Methyl-2-pyrrolidone | 96.5 |
| Coco fatty acid diethanolamide | 0.5 |
| (coco fatty acid:diethanolamine = 1:1) | |

Formulation Example 2

| | Percent by weight |
|---|---|
| 4,5-Dichloro-1,2-dithiol-3-one | 6.0 |
| Bromonitrostyrene | 1.5 |
| N-Methyl-2-pyrrolidone | 92.0 |
| Coco fatty acid diethanolamide | 0.5 |

Formulation Example 3

| | Percent by weight |
|---|---|
| 4,5-Dichloro-1,2-dithiol-3-one | 1.0 |
| Bromonitrostyrene | 9.0 |
| N-Methyl-2-pyrrolidone | 89.5 |
| Coco fatty acid diethanolamide | 0.5 |

While the present invention has been described by the foregoing specification including working examples and test examples, the embodiment described herein can be changed and modified in various manners within the scope and the spirit of this invention.

What is claimed is:

1. A composition having microbicidal and microbistatic activity against microorganisms selected from the group consisting of Gram positive bacteria, Gram negative bacteria and yeasts, said composition comprising 4,5-dichloro-1,2-dithiol-3-one and bromonitrostyrene in a Synergistic weight ratio of 9:1 to 1:19.

2. A composition as claimed in claim 1, wherein the weight ratio of 4,5-dichloro-1,2-dithiol-3-one and bromonitrostyrene is 4:1 to 1:9.

3. A composition as claimed in claim 1, wherein said 4,5-dichloro-1,2-dithiol-3-one and said bromonitrostyrene are dissolved in an organic solvent.

4. A composition as claimed in claim 3, wherein said 4,5-dichloro-1,2-dithiol-3-one and said bromonitrostyrene are dissolved in a solvent selected from the group consisting of N-methyl-2-pyrrolidone, dimethylformamide, mono- and polyalkylene glycols, mono- and polyalkylene glycol monomethyl ethers and mixtures thereof.

5. A composition as claimed in claim 1, wherein said 4,5-dichloro-1,2-dithiol-3one and said bromonitrostyrene are dissolved or dispersed in a solvent selected from the group consisting of a liquid carrier organic solvent, water, and mixtures thereof, wherein said solvent contains a dispersant, an emulsifier or a stabilizer.

6. A method of killing or inhibiting the growth of microorganisms selected from the group consisting of Gram positive bacteria, Gram negative bacteria and yeasts in industrial materials or in water systems which comprises the step of treating the material or water with the composition as claimed in claim 9 in an amount sufficient to kill or inhibit growth of the microorganisms.

7. A method of killing or inhibiting the growth of microorganisms selected from the group consisting of Gram positive bacteria, Gram negative bacteria and yeasts in paper mill white water systems or cooling tower water systems to thereby control slime formation in said systems which comprises the step of treating the water systems with the composition as claimed in claim 1 in an amount sufficient to kill or inhibit growth of the microorganisms.

* * * * *